US012605311B2

(12) United States Patent
Hamada et al.

(10) Patent No.: US 12,605,311 B2
(45) Date of Patent: Apr. 21, 2026

(54) HYDROGEL STRUCTURE

(71) Applicant: Kao Corporation, Tokyo (JP)

(72) Inventors: Saki Hamada, Wakayama (JP); Shohei Toyota, Tokyo (JP)

(73) Assignee: KAO CORPORATION, Tokyo (JP)

( * ) Notice: Subject to any disclaimer, the term of this patent is extended or adjusted under 35 U.S.C. 154(b) by 424 days.

(21) Appl. No.: 18/275,832

(22) PCT Filed: Feb. 5, 2021

(86) PCT No.: PCT/JP2021/004420
§ 371 (c)(1),
(2) Date: Aug. 4, 2023

(87) PCT Pub. No.: WO2022/168285
PCT Pub. Date: Aug. 11, 2022

(65) Prior Publication Data
US 2024/0122819 A1 Apr. 18, 2024

(51) Int. Cl.
*A61K 8/04* (2006.01)
*A61K 8/73* (2006.01)
*C08J 3/075* (2006.01)

(52) U.S. Cl.
CPC ................ *A61K 8/042* (2013.01); *A61K 8/73* (2013.01); *C08J 3/075* (2013.01); *C08J 2305/12* (2013.01)

(58) Field of Classification Search
CPC .. A61K 8/042; A61K 8/73; C08J 3/075; C08J 2305/12
See application file for complete search history.

(56) References Cited

U.S. PATENT DOCUMENTS

| | | | | | |
|---|---|---|---|---|---|
| 7,776,240 | B2 * | 8/2010 | Chu | ........................ | A61P 37/04 264/4.1 |
| 2002/0034525 | A1 * | 3/2002 | Sakai | ................... | B01J 13/0056 424/401 |
| 2008/0274161 | A1 | 11/2008 | Muratoglu et al. | | |
| 2009/0155323 | A1 | 6/2009 | Sakai et al. | | |
| 2010/0015186 | A1 * | 1/2010 | Takagi | ................... | A61Q 15/00 424/59 |

(Continued)

FOREIGN PATENT DOCUMENTS

| | | |
|---|---|---|
| EP | 1 172 083 A2 | 1/2002 |
| JP | 10-99030 A | 4/1998 |

(Continued)

OTHER PUBLICATIONS

International Preliminary Report on Patentability and English translation of the Written Opinion of the International Searching Authority for International Application No. PCT/JP2021/004420, dated Aug. 17, 2023.

(Continued)

*Primary Examiner* — Blessing M Fubara
(74) *Attorney, Agent, or Firm* — Birch, Stewart, Kolasch & Birch, LLP

(57) ABSTRACT

A hydrogel structure (10) includes: a continuous phase (11) of a first hydrogel; and a dispersion phase (12) of a second hydrogel, the dispersion phase being dispersed in the continuous phase (11). A ratio of a local minimum value of a load after break to a breaking load (a local minimum value of a load after break/a breaking load) of the hydrogel structure (10) is 0.1 or more.

23 Claims, 1 Drawing Sheet

(56) References Cited

U.S. PATENT DOCUMENTS

| 2013/0028972 | A1 | 1/2013 | Schwier et al. | |
|---|---|---|---|---|
| 2013/0142853 | A1 | 6/2013 | Matsuo et al. | |
| 2014/0309314 | A1* | 10/2014 | Sahouani | C08F 2/16 |
| | | | | 526/312 |
| 2016/0166504 | A1 | 6/2016 | Jarrett et al. | |
| 2016/0199306 | A1 | 7/2016 | Schwier et al. | |
| 2018/0369149 | A1 | 12/2018 | Schwier et al. | |
| 2019/0269621 | A1 | 9/2019 | Schwier et al. | |
| 2020/0338218 | A1 | 10/2020 | Mochizuki et al. | |

FOREIGN PATENT DOCUMENTS

| JP | 2002-159838 | A | 6/2002 |
|---|---|---|---|
| JP | 2008-540809 | A | 11/2008 |
| JP | 2009-118811 | A | 6/2009 |
| JP | 2014-524926 | A | 9/2014 |
| JP | 2017-537130 | A | 12/2017 |
| WO | WO2007/066635 | A1 | 6/2007 |
| WO | WO2019/088292 | A1 | 5/2019 |

OTHER PUBLICATIONS

Extended European Search Report for European Application No. 21924679.0, dated Sep. 10, 2024.
International Search Report for PCT/JP2021/004420 mailed on Apr. 27, 2021.

* cited by examiner

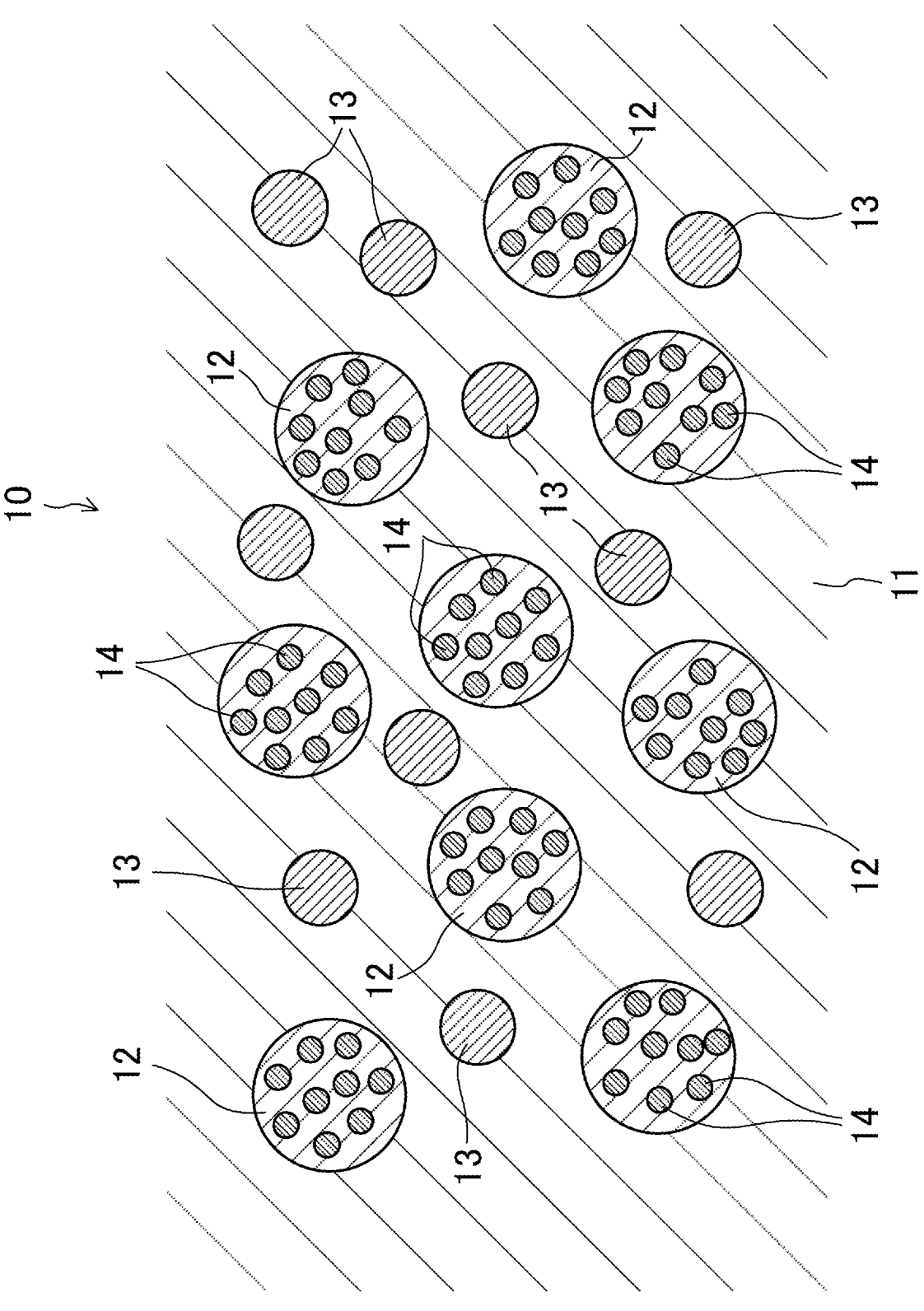

HYDROGEL STRUCTURE

TECHNICAL FIELD

The present invention relates to a hydrogel structure, a method for producing the same, a cosmetic product composition containing the same, and use of the same as a cosmetic product.

BACKGROUND ART

For cosmetic products, drugs, quasi drugs, food products, and the like, a hydrogel is widely used. For example, Patent Document 1 discloses a form in which a seamless capsule having an outer film formed from agar or the like is dispersed in a gummy material containing gelatin. Patent Document 2 discloses a hydrogel particle in which a dispersion phase of an oily component is dispersed in a continuous phase of a hydrogel. Patent Document 3 discloses a jelly food product in which hydrogel particles are dispersed in a hydrogel.

CITATION LIST

Patent Documents

Patent Document 1: Japanese Unexamined Patent Publication No. 2009-118811
Patent Document 2: Japanese Unexamined Patent Publication No. 2002-159838
Patent Document 3: Japanese Unexamined Patent Publication No. H10-99030

SUMMARY OF THE INVENTION

The present invention is a hydrogel structure including: a continuous phase of a first hydrogel; and a dispersion phase of a second hydrogel, the dispersion phase being dispersed in the continuous phase, a ratio of a local minimum value of a load after break to a breaking load (a local minimum value of load after break/breaking load) being 0.1 or more.

The present invention is a hydrogel structure including: a continuous phase of a first hydrogel; and a dispersion phase of a second hydrogel, the dispersion phase being dispersed in the continuous phase, a mass ratio of the dispersion phase to the continuous phase (dispersion phase/continuous phase) being more than 1/99.

The present invention is directed to a cosmetic product composition containing the hydrogel structure of the present invention.

The present invention is further directed to the use of the hydrogel structure of the present invention as a cosmetic product.

The present invention is further directed to a method for producing the hydrogel structure of the present invention, including dispersing hydrogel particles that become the dispersion phase of the second hydrogel in an aqueous first gel agent solution for forming the continuous phase of the first hydrogel; and then gelling the first aqueous gel agent solution.

The present invention is further directed to a method for producing a hydrogel structure, including: dispersing a second hydrogel in a first aqueous gel agent solution for forming a continuous phase of a first hydrogel; and gelling the first gel agent solution, a temperature of the first aqueous gel agent solution during the dispersion of the second hydrogel being equal to or higher than a solidification point of the aqueous first gel agent solution and lower than a melting point of the second hydrogel.

BRIEF DESCRIPTION OF THE DRAWING

FIG. 1 is a schematic view of a hydrogel structure according to an embodiment.

DESCRIPTION OF EMBODIMENTS

Hereinafter, embodiments will be described in detail.

FIG. 1 illustrates a hydrogel structure 10 according to an embodiment. The hydrogel structure 10 according to the embodiment can be used, for example, for cosmetic products, drugs, quasi drugs, food products, and the like, and in particular, can be suitably used as a component contained in a cosmetic product composition.

The hydrogel structure 10 according to the embodiment includes a continuous phase 11 and a dispersion phase A12 dispersed in the continuous phase 11.

For example, a cosmetic product such as a milky lotion is usually taken in an appropriate amount and spread on the palm during use. When the cosmetic product includes a hydrogel, the hydrogel is crushed on the palm. However, the hydrogel that has a high gel strength has a problem that the hydrogel is unlikely to be crushed on the palm and it takes a time to crush the hydrogel. As a countermeasure for this, it is considered that the gel strength of the hydrogel is decreased by increasing a moisture content. In this case, a larger amount of water is separated from the hydrogel. It is also considered that the gel strength is decreased by adding oil or powder. In this case, addition of such an unnecessary component cannot be avoided.

However, the hydrogel structure 10 according to the embodiment includes the dispersion phase A12 of a second hydrogel, dispersed in the continuous phase 11 of a first hydrogel, and therefore excellent disintegration properties can be achieved. Although the reason why the hydrogel structure 10 according to the embodiment exhibits such an effect is not certain, it is considered as follows. The hydrogel structure 10 is difficult to be elastically deformed before disintegration due to the presence of the dispersion phase A12; thus, excellent disintegration properties can be achieved with a breaking load being kept within a range capable of achieving storage stability of the hydrogel structure 10.

The content of the continuous phase 11 in the hydrogel structure 10 is suitably 20 mass % or more, more suitably 30 mass % or more, yet more suitably 40 mass % or more from the viewpoint of achieving storage stability of the hydrogel structure, and is suitably 80 mass % or less, more suitably 70 mass % or less, yet more suitably 60 mass % or less from the viewpoint of achieving excellent disintegration properties of the hydrogel structure.

The continuous phase 11 is formed from the first hydrogel. The "hydrogel" herein refers to a gel made from a gel agent and water, and may be a gel resulting from the thermal reversibility of a sol-gel as in a situation where the gel agent is agar, for example. The "gel agent" herein refers to a water-soluble organic compound, in which an aqueous solution of the water-soluble organic compound dissolved in water causes a sol-gel transition at a gel point (solidification point). Therefore when the first hydrogel is made from a first gel agent and water, the continuous phase 11 is formed by producing the first hydrogel from a first aqueous gel agent solution containing the first gel agent at a temperature lower than the gel point.

The first gel agent contains a water-soluble polymer. Examples of the water-soluble polymer include water-soluble uncrosslinked polymers such as agar, carrageenan, gellan gum, xanthan gum, and high methoxyl pectin. From the viewpoint of achieving excellent disintegration properties of the hydrogel structure, the first gel agent contains suitably a water-soluble uncrosslinked polymer, more suitably one or more types selected from the group consisting of agar, carrageenan, gellan gum, xanthan gum, and high methoxyl pectin, and yet more suitably agar. The "agar" herein refers to a hemicellulose containing galactan including 1,3-bond and 1,4-bond of galactose.

The jelly strength of the first gel agent is, for example, from 19.6 kPa (200 g/cm$^2$) to 147 kPa (1500 g/cm$^2$) inclusive. Herein, the jelly strength of the gel agent may be determined by the Nikkansui's measuring method. Specifically, a 1.5 mass % aqueous gel agent solution is prepared, left to stand at 20° C. for 15 hours, and solidified to give a hydrogel, and a load is applied to the hydrogel with a Nikkansui's jelly strength measuring device (available from KIYA Seisakusho Co. Ltd.). The jelly strength of the gel agent is the maximum mass (g) per surface area of 1 cm$^2$ when the hydrogel can withstand the load at 20° C. for 20 seconds.

The content of the first gel agent in the continuous phase 11 is suitably 0.8 mass % or more, more suitably 1.0 mass % or more, yet more suitably 1.2 mass % or more from the viewpoint of ensuring storage stability of the hydrogel structure, and is suitably 20 mass % or less, more suitably 15 mass % or less, yet more suitably 10 mass % or less, still more suitably 6 mass % or less from the viewpoint of achieving excellent disintegration properties of the hydrogel structure.

The continuous phase 11 may contain an emulsifying dispersant. Examples of the emulsifying dispersant include a polymer emulsifying dispersant, a nonionic surfactant, an anionic surfactant, a cationic surfactant, and an amphoteric surfactant. The emulsifying dispersant suitably contains one or two or more of these.

The content of the emulsifying dispersant in the continuous phase 11 is suitably 0.1 mass % or more, more suitably 0.5 mass % or more, yet more suitably 1 mass % or more from the viewpoint of ensuring storage stability of the hydrogel structure, and is suitably 10 mass % or less, more suitably 5 mass % or less, yet more suitably 2 mass % or less from the same viewpoint.

In addition, the continuous phase 11 may further contain a water-soluble vitamin B or C, a humectant, an antiperspirant, an antimicrobial agent, a disinfectant, or the like.

The breaking load of the continuous phase 11 is suitably 0.1 N or more, more suitably 1 N or more, yet more suitably 5 N or more from the viewpoint of achieving storage stability of the hydrogel structure, and is suitably 30 N or less, more suitably 20 N or less, yet more suitably 15 N or less from the viewpoint of achieving excellent disintegration properties of the hydrogel structure. This breaking load is measured by a method described in the Examples below.

The mass ratio of the dispersion phase A12 to the continuous phase 11 in the hydrogel structure 10 (the dispersion phase A12/the continuous phase 11) is more than 1/99, suitably 3/97 or more, more suitably 13/87 or more, yet more suitably 15/85 or more from the viewpoint of achieving excellent disintegration properties of the hydrogel structure, and is suitably 99/1 or less, more suitably 80/20 or less, yet more suitably 40/60 or less, and still more suitably 25/75 or less from the viewpoint of achieving storage stability of the hydrogel structure.

The content of the dispersion phase A12 in the hydrogel structure 10 is suitably 3 mass % or more, more suitably 13 mass % or more, yet more suitably 20 mass % or more, still more suitably 30 mass % or more, still more suitably 40 mass % or more from the viewpoint of achieving excellent disintegration properties of the hydrogel structure, and is suitably 99 mass % or less, more suitably 90 mass % or less, yet more suitably 80 mass % or less, still more suitably 70 mass % or less, still more suitably 60 mass % or less from the viewpoint of achieving storage stability of the hydrogel structure.

The dispersion phase A12 is formed from the second hydrogel. When the second hydrogel is obtained from a second gel agent and water, the dispersion phase A12 is formed by producing the second hydrogel from a second aqueous gel agent solution containing the second gel agent at a temperature lower than the gel point. The melting point of the dispersion phase A12 is suitably higher than the solidification point of the first aqueous gel agent solution, for example, 85° C. to 95° C., from the viewpoint of ensuring storage stability of the hydrogel structure.

Examples of the second gel agent include those shown as examples of the first gel agent. From the viewpoint of achieving excellent disintegration properties of the hydrogel structure, the second gel agent contains suitably one or more types of these, more suitably agar. The second gel agent may be the same as or different from the first gel agent.

The jelly strength of the second gel agent and the gel point (solidification point) of the second aqueous gel agent solution are the same as the jelly strength of the first gel agent and the gel point of the first aqueous gel agent solution, respectively.

The content of the second gel agent in the dispersion phase A12 is suitably 0.8 mass % or more, more suitably 1.0 mass % or more, yet more suitably 1.2 mass % or more from the viewpoint of ensuring storage stability of the hydrogel structure, and is suitably 10 mass % or less, more suitably 8 mass % or less, yet more suitably 6 mass % or less from the viewpoint of achieving excellent disintegration properties of the hydrogel structure.

The second gel agent may be the same as the first gel agent. In this case, the content of the second gel agent in the dispersion phase A12 may be the same as the content of the first gel agent in the continuous phase 11. That is, the composition of the first hydrogel may be the same as the composition of the second hydrogel.

The dispersion phase A12 may contain an emulsifying dispersant. Examples of the emulsifying dispersant include those shown as examples of the emulsifying dispersant in the continuous phase 11. The suitable content of the emulsifying dispersant in the dispersion phase A12 is also the same as that in the continuous phase 11.

The composition of the dispersion phase A12 may be the same as or different from the composition of the continuous phase 11. In addition, similarly to the continuous phase 11, the dispersion phase A12 may contain a water-soluble vitamin B or C, a humectant, an antiperspirant, an antimicrobial agent, a disinfectant, or the like.

For example, the dispersion phase A12 may have a particulate shape such as a spherical shape, a plate shape, or a needle shape. The "spherical shape" herein includes not only a true spherical shape but also a nearly spherical shape such as an ellipsoidal shape, which may have an uneven surface. The average particle diameter of the dispersion phase A12 is suitably 1 µm or more, more suitably 5 µm or more, yet more suitably 10 µm or more from the viewpoint of achieving excellent disintegration properties and storage stability, and is suitably 5 mm or less, more suitably 3 mm or less, yet more suitably 2 mm or less from the viewpoint of achieving favorable touch when the hydrogel structure is applied to the skin. The average particle diameter of the dispersion phase A12 is a volume-based average particle diameter that is measured with a laser diffraction/scattering particle size distribution measuring device (e.g., LA-960 available from Horiba, Ltd.) by a laser diffraction and scattering method.

The breaking load of the dispersion phase A12 is suitably 0.1 N or more, more suitably 1 N or more, yet more suitably 5 N or more from the viewpoint of achieving excellent disintegration properties of the hydrogel structure, and is suitably 30 N or less, more suitably 20 N or less, yet more suitably 15 N or less from the same viewpoint. This breaking load is measured by a method described in the Examples below.

The content of the first gel agent and the second gel agent in the hydrogel structure is suitably 0.8 mass % or more, more suitably 1.0 mass % or more, yet more suitably 1.2 mass % or more from the viewpoint of ensuring storage stability of the hydrogel structure, and is suitably 20 mass % or less, more suitably 15 mass % or less, yet more suitably 10 mass % or less, still more suitably 6 mass % or less from the viewpoint of achieving excellent disintegration properties of the hydrogel structure.

The content of the emulsifying dispersant in the hydrogel structure 10 is suitably 0.1 mass % or more, more suitably 0.3 mass % or more, yet more suitably 0.5 mass % or more from the viewpoint of ensuring storage stability of the hydrogel structure, and is suitably 5 mass % or less, more suitably 3 mass % or less, yet more suitably 1 mass % or less from the same viewpoint.

The hydrogel structure 10 according to the embodiment may include dispersion particles B13 different from the dispersion phase A12 dispersed in the continuous phase 11.

Examples of the dispersion particles B13 include a low-water soluble cosmetic product component. Examples of such a low-water soluble cosmetic product component include an oily component for a cosmetic product such as a silicone oil, ceramide, and a fat-soluble vitamin; and a powder for a cosmetic product such as titanium oxide, zinc oxide, and a pigment. The dispersion particles B13 suitably contain one or more types of them. The "low-water soluble" herein means that the degree of solubility in water at 20° C. is 1 mass % or less.

The content of the dispersion particles B13 in the hydrogel structure 10 is suitably 0.1 mass % or more, more suitably 1 mass % or more, yet more suitably 10 mass % or more from the viewpoint of using the hydrogel structure as a cosmetic product, and is suitably 50 mass % or less, more suitably 40 mass % or less, yet more suitably 30 mass % or less from the viewpoint of ensuring storage stability of the hydrogel structure.

For example, the dispersion particles B13 may have a particulate shape such as a spherical shape, a plate shape, or a needle shape. The average particle diameter of the dispersion particles B13 is suitably 0.1 μm or more, more suitably 1 μm or more, yet more suitably 5 μm or more from the viewpoint of ensuring emulsification stability, and is suitably 100 μm or less, more suitably 50 μm or less, yet more suitably 20 μm or less from the same viewpoint. The average particle diameter of the dispersion particles B13 is also a volume average particle diameter. The average particle diameter of the dispersion particles B13 is suitably smaller than the average particle diameter of the dispersion phase A12.

The hydrogel structure 10 according to the embodiment may include dispersion particles C14 that are dispersed in the dispersion phase A12. The kind, content, shape, and size of the dispersion particles C14 may be the same as those of the dispersion particles B13.

For example, the hydrogel structure 10 according to the embodiment may have a particulate shape such as a spherical shape, a plate shape, or a needle shape. The maximum diameter of the hydrogel structure 10 is suitably 500 μm or more, more suitably 1 mm or more, yet more suitably 5 mm or more, still more suitably 10 mm or more from the viewpoint of ensuring easy blending and dispersion stability of the dispersion phase A12, and is suitably 40 mm or less, more suitably 30 mm or less, yet more suitably 20 mm or less from the viewpoint of easy molding and easy handling of the hydrogel structure 10. The "maximum diameter" herein means the maximum value of dimension allowable in the hydrogel structure. When the hydrogel structure has an ellipsoidal shape, the "maximum diameter" means the length of long axis of the hydrogel structure. When the hydrogel structure has a spherical shape, the "maximum diameter" means the diameter of the hydrogel structure. When the hydrogel structure 10 alone is used in a paste form, the maximum diameter of the hydrogel structure 10 is suitably from 500 μm to 1 mm inclusive from the viewpoint of ensuring flowability of a paste preparation. When the hydrogel structure 10 is blended in a preparation for use, the maximum diameter of the hydrogel structure 10 is suitably from 500 μm to 5 mm inclusive from the viewpoint of dispersion stability of the hydrogel structure 10.

The ratio of the maximum diameter of the hydrogel structure 10 to the average particle diameter of the dispersion phase A12 is suitably 1 or more, more suitably 5 or more, yet more suitably 10 or more from the viewpoint of ensuring easy blending and dispersion stability of the dispersion phase A12, and is suitably 50000 or less, more suitably 10000 or less, yet more suitably 1000 or less, still more suitably 800 or less, still more suitably 700 or less from the viewpoint of easy molding and easy handling of the hydrogel structure 10.

The breaking load of the hydrogel structure 10 according to the embodiment is suitably 0.1 N or more, more suitably 0.3 N or more, yet more suitably 0.5 N or more from the viewpoint of ensuring storage stability of the hydrogel structure, and is suitably 30 N or less, more suitably 20 N or less, yet more suitably 15 N or less, still more suitably 10 N or less, still more suitably 5 N or less from the viewpoint of achieving excellent disintegration properties of the hydrogel structure. The ratio of the local minimum value of the load after break to the breaking load (the local minimum value of the load after break/the breaking load) of the hydrogel structure 10 according to the embodiment is 0.1 or more, suitably 0.2 or more, more suitably 0.33 or more from the viewpoint of achieving excellent disintegration properties of the hydrogel structure, and is suitably 1 or less, more suitably 0.95 or less, yet more suitably 0.9 or less from the viewpoint of ensuring storage stability of the hydrogel structure.

The breaking distortion factor of the hydrogel structure 10 according to the embodiment is suitably 1% or more, more suitably 3% or more, yet more suitably 5% or more from the viewpoint of ensuring storage stability of the hydrogel structure, and is suitably 50% or less, more suitably 45% or less, yet more suitably 40% or less, still more suitably 35% or less from the viewpoint of achieving excellent disintegration properties of the hydrogel structure. The breaking load, the local minimum value of the load after break, and the breaking distortion factor can be measured, for example, by texture measurement under a condition of 25° C. with a texture tester.

In the texture measurement, a texture curve representing a relationship between a compression distance and a load is obtained. In this texture curve, the load increases with an increase in the compression distance of the hydrogel structure, and a peak of the load is exhibited when the hydrogel structure is broken. The breaking load and the breaking distortion factor are determined from the peak load and the compression distance at this time. In the texture curve, when the compression distance of the hydrogel structure further increases after breakage of the hydrogel structure, one or more local minimum values of the load are exhibited with a change in the form of a hydrogel structure broken. When the elastic properties of the hydrogel structure finally broken are lost, a rising edge of the load is exhibited. When there is one local minimum value of the load, the local minimum value of the load after break is determined from the local minimum value of the load at that time. When there are a plurality of local minimum values of the load, the local minimum value of the load after break is determined from the most minimum value. There is suitably one local minimum value of the load after break of the hydrogel structure in the texture curve from the viewpoint of achieving favorable comfort during use when the hydrogel structure is used for a cosmetic product or the like.

Next, a method for producing the hydrogel structure 10 according to the embodiment will be described.

The second aqueous gel agent solution for forming the dispersion phase A12 is prepared. In order to disperse the dispersion particles C14 in the dispersion phase A12, the dispersion particles C14 are dispersed in the second aqueous gel agent solution in advance. This second aqueous gel agent solution is used to produce hydrogel particles that become the dispersion phase A12 of the second hydrogel.

Examples of a method for producing the hydrogel particles include a dropping method, a spraying method, a stirring method, a crushing method, and a stirring and cooling method. The dropping method is such that the second aqueous gel agent solution is discharged from a hole to form droplets using a property in which the second aqueous gel agent solution forms droplets by its surface tension or interfacial tension, and the droplets are cooled and solidified in a gas phase such as air or a liquid phase to produce the hydrogel. The spraying method is such that the second aqueous gel agent solution is sprayed into a gas phase from a spray nozzle, to form droplets due to its surface tension, and the droplets are cooled and solidified in the gas phase to produce the hydrogel. The stirring method is such that while the second aqueous gel agent solution is added to a liquid having no substantial miscibility therewith and a temperature adjusted to be higher than the gel point thereof, the second aqueous gel agent solution is pulverized by a shear force caused by stirring, and droplets are cooled and solidified in the liquid having no substantial miscibility therewith using a property in which the second aqueous gel agent solution forms droplets by its interfacial tension, to produce the hydrogel. The crushing method is such that an aggregated solid obtained by cooling and solidifying the second aqueous gel agent solution is mechanically crushed. The stirring and cooling method is such that the second aqueous gel agent solution is stirred until the temperature reaches equal to or lower than the gel point, to produce the hydrogel particles.

Subsequently, the first aqueous gel agent solution for forming the continuous phase 11 of the first hydrogel is prepared. In order to disperse the dispersion particles B13 in the continuous phase 11, the dispersion particles B13 are dispersed in the first aqueous gel agent solution in advance.

A predetermined amount of the hydrogel particles is added to and dispersed in the first aqueous gel agent solution, and the fluid dispersion thus obtained is then cooled, resulting in gelation. Thus, the hydrogel structure 10 according to the embodiment can be obtained. When the first gel agent and the second gel agent are agar, the temperature of the first aqueous gel agent solution at which the hydrogel particles are added and dispersed is suitably equal to or higher than the solidification point of the first aqueous gel agent solution and lower than the melting point of the hydrogel particles, more suitably from 40° C. to 80° C. inclusive, yet more suitably from 45° C. to 75° C. inclusive, still more suitably from 50° C. to 70° C. inclusive from the viewpoint of maintaining a sol state of the first aqueous first gel agent solution and avoiding re-solation of the hydrogel particles. When the fluid dispersion obtained by adding the hydrogel particles to the first aqueous gel agent solution is poured into a mold before cooling, and cooled in the mold, resulting in gelation, the hydrogel structure 10 can be molded into a shape. When a solid obtained by cooling the fluid dispersion obtained by adding the hydrogel particles to the first aqueous gel agent solution is mechanically crushed, the hydrogel structure 10 can be given a shape. In the dropping method, the spraying method, the stirring method, the crushing method, or the stirring and cooling method, a fluid dispersion obtained by adding the hydrogel particles to the aqueous first gel agent solution instead of the second aqueous gel agent solution can be used, to form the hydrogel structure 10 according to the embodiment into particles.

As for the above-mentioned embodiment, the following configurations are further disclosed.

<1> A hydrogel structure including: a continuous phase of a first hydrogel; and a dispersion phase of a second hydrogel, the dispersion phase being dispersed in the continuous phase, a ratio of a local minimum value of a load after break to a breaking load (a local minimum value of load after break/a breaking load) being 0.1 or more.

<2> A hydrogel structure including: a continuous phase of a first hydrogel; and a dispersion phase of a second hydrogel, the dispersion phase being dispersed in the continuous phase, a mass ratio of the dispersion phase to the continuous phase (the dispersion phase/the continuous phase) being more than 1/99.

<3> The hydrogel structure of <1> or <2>, wherein a mass ratio of the dispersion phase to the continuous phase (the dispersion phase/the continuous phase) is suitably 3/97 or more, more suitably 13/87 or more, yet more suitably 15/85 or more, and suitably 99/1 or less, more suitably 80/20 or less, yet more suitably 40/60 or less, still more suitably 25/75 or less. 20<4> The hydrogel structure of <1> or <2>, wherein a mass ratio of the dispersion phase to the continuous phase (the dispersion phase/the continuous phase) is 99/1 or less.

<5> The hydrogel structure of <4>, wherein the mass ratio of the dispersion phase to the continuous phase (the dispersion phase/the continuous phase) is from 3/97 to 80/20 inclusive.

<6> The hydrogel structure of <4>, wherein the mass ratio of the dispersion phase to the continuous phase (the dispersion phase/the continuous phase) is from 15/85 to 80/20 inclusive.

<7> The hydrogel structure of any one of <1> to <6>, wherein the hydrogel structure has a maximum diameter of suitably 500 μm or more, more suitably 1 mm or more, yet more suitably 5 mm or more, still more suitably 10 mm or more, and suitably 40 mm or less, more suitably 30 mm or less, yet more suitably 20 mm or less.

<8> The hydrogel structure of any one of <1> to <7>, wherein a content of the continuous phase in the hydrogel structure is suitably 20 mass % or more, more suitably 30 mass % or more, yet more suitably 40 mass % or more, and suitably 80 mass % or less, more suitably 70 mass % or less, yet more suitably 60 mass % or less.

<9> The hydrogel structure of any one of <1> to <8>, wherein a first gel agent used to obtain the first hydrogel suitably contains a water-soluble uncrosslinked polymer, more suitably one or more types selected from the group consisting of agar, carrageenan, gellan gum, xanthan gum, and high methoxyl pectin, further suitably agar.

<10> The hydrogel structure of any one of <1> to <9>, wherein a content of the first gel agent in the continuous phase is suitably 0.8 mass % or more, more suitably 1.0 mass % or more, yet more suitably 1.2 mass % or more, and suitably 20 mass % or less, more suitably 15 mass % or less, yet more suitably 10 mass % or less, still more suitably 6 mass % or less.

<11> The hydrogel structure of any one of <1> to <10>, wherein one or both of the continuous phase and the dispersion phase contain an emulsifying dispersant.

<12> The hydrogel structure of <10>, wherein a content of the emulsifying dispersant in the continuous phase or the dispersion phase is suitably 0.1 mass % or more, more suitably 0.5 mass % or more, yet more suitably 1 mass % or more, and suitably 10 mass % or less, more suitably 5 mass % or less, yet more suitably 2 mass % or less.

<13> The hydrogel structure of <11> or <12>, wherein a content of the emulsifying dispersant in the hydrogel structure is suitably 0.1 mass % or more, more suitably 0.3 mass % or more, yet more suitably 0.5 mass % or more, and suitably 5 mass % or less, more suitably 3 mass % or less, yet more suitably 1 mass % or less.

<14> The hydrogel structure of any one of <1> to <13>, wherein the breaking load of the continuous phase is suitably 0.1 N or more, more suitably 1 N or more, yet more suitably 5 N or more, and suitably 30 N or less, more suitably 20 N or less, yet more suitably 15 N or less.

<15> The hydrogel structure of any one of <1> to <14>, wherein a content of the dispersion phase in the hydrogel structure is suitably 3 mass % or more, more suitably 13 mass % or more, yet more suitably 20 mass % or more, still more suitably 30 mass % or more, still more suitably 40 mass % or more, and suitably 99 mass % or less, more suitably 90 mass % or less, yet more suitably 80 mass % or less, still more suitably 70 mass % or less, still more suitably 60 mass % or less.

<16> The hydrogel structure of any one of <1> to <15>, wherein a second gel agent used to obtain the second hydrogel suitably contains a water-soluble uncrosslinked polymer, more suitably one or more types selected from the group consisting of agar, carrageenan, gellan gum, xanthan gum, and high methoxyl pectin, and further suitably agar.

<17> The hydrogel structure of any one of <1> to <16>, wherein a gel agent used to obtain the first hydrogel is the same as a gel agent used to obtain the second hydrogel.

<18> The hydrogel structure of any one of <1> to <17>, wherein a content of a second gel agent in the dispersion phase is suitably 0.8 mass % or more, more suitably 1.0 mass % or more, yet more suitably 1.2 mass % or more, and suitably 10 mass % or less, more suitably 8 mass % or less, yet more suitably 6 mass % or less.

<19> The hydrogel structure of any one of <1> to <18>, wherein composition of the first hydrogel is the same as composition of the second hydrogel.

<20> The hydrogel structure of any one of <1> to <19>, wherein an average particle diameter of the dispersion phase is suitably 1 μm or more, more suitably 5 μm or more, yet more suitably 10 μm or more, and suitably 5 mm or less, more suitably 3 mm or less, yet more suitably 2 mm or less.

<21> The hydrogel structure of any one of <1> to <20>, wherein the breaking load of the dispersion phase is suitably 0.1 N or more, more suitably 1 N or more, yet more suitably 5 N or more, and suitably 30 N or less, more suitably 20 N or less, yet more suitably 15 N or less.

<22> The hydrogel structure of any one of <1> to <21>, wherein a content of a first gel agent and a second gel agent in the hydrogel structure is suitably 0.8 mass % or more, more suitably 1.0 mass % or more, yet more further suitably 1.2 mass % or more, and suitably 20 mass % or less, more suitably 15 mass % or less, yet more suitably 10 mass % or less, still more suitably 6 mass % or less.

<23> The hydrogel structure of any one of <1> to <22>, further including dispersion particles different from the dispersion phase dispersed in the continuous phase.

<24> The hydrogel structure of <23>, wherein the dispersion particles are a low-water soluble cosmetic product component.

<25> The hydrogel structure of <23> or <24>, wherein a content of the dispersion particles in the hydrogel structure is suitably 0.1 mass % or more, more suitably 1 mass % or more, yet more suitably 10 mass % or more, and suitably 50 mass % or less, more suitably 40 mass % or less, yet more suitably 30 mass % or less.

<26> The hydrogel structure of any one of <23> to <25>, wherein an average particle diameter of the dispersion particles is suitably 0.1 μm or more, more suitably 1 μm or more, yet more suitably 5 μm or more, and suitably 100 μm or less, more suitably 50 μm or less, yet more suitably 20 μm or less.

<27> The hydrogel structure of any one of <23> to <26>, wherein an average particle diameter of the dispersion particles is smaller than the average particle diameter of the dispersion phase.

<28> The hydrogel structure of any one of <1> to <27>, wherein the breaking load of the hydrogel structure is suitably 0.1 N or more, more suitably 0.3 N or more, yet more suitably 0.5 N or more, and suitably 30 N or less, more suitably 20 N or less, yet more suitably 15 N or less, still more suitably 10 N or less, still more suitably 5 N or less.

<29> The hydrogel structure of any one of <1> to <28>, wherein the ratio of the local minimum value of the load after break to the breaking load (the local minimum value of load after break/the breaking load) of the hydrogel structure is suitably 0.2 or more, more suitably 0.33 or more.

<30> The hydrogel structure of any one of <1> to <29>, wherein the ratio of the local minimum value of the load after break to the breaking load (the local minimum value of load after break/the breaking load) of the hydrogel structure is suitably 1 or less, more suitably 0.95 or less, yet more suitably 0.9 or less.

<31> The hydrogel structure of any one of <1> to <30>, wherein a breaking distortion factor of the hydrogel structure is suitably 1% or more, more suitably 3% or more, yet more suitably 5% or more, and suitably 50% or less, more suitably 45% or less, yet more suitably 40% or less, still more suitably 35% or less.

<32> The hydrogel structure of any one of <1> to <31>, wherein the hydrogel structure suitably has a particulate shape, more suitably a spherical shape.

<33> The hydrogel structure of any one of <1> to <32>, wherein a ratio of a maximum diameter of the hydrogel structure to an average particle diameter of the dispersion phase is suitably 1 or more, more suitably 5 or more, yet more suitably 10 or more, and suitably 50000 or less, more suitably 10000 or less, yet more suitably 1000 or less, still more suitably 800 or less, still more suitably 700 or less.

<34> A cosmetic product composition containing the hydrogel structure of any one of <1> to <33>.

<35> Use of the hydrogel structure of any one of <1> to <33> as a cosmetic product.

<36> A method for producing the hydrogel structure of any one of <1> to <33> including: dispersing hydrogel particles that become the dispersion phase of the second hydrogel in a first aqueous gel agent solution for forming the continuous phase of the first hydrogel; and gelling the first aqueous gel agent solution.

<37> The method for producing the hydrogel structure of <36>, wherein a first gel agent used to obtain the first hydrogel and a second gel agent used to obtain the second hydrogel are agar, and a temperature of the first aqueous gel agent solution at which the hydrogel particles are dispersed is suitably equal to or higher than a solidification point of the first aqueous gel agent solution and lower than a melting point of the hydrogel particles, more suitably from 40° C. to 80° C. inclusive, yet more suitably from 45° C. to 75° C. inclusive, still more suitably from 50° C. to 70° C. inclusive.

<38> A method for producing a hydrogel structure including: dispersing a second hydrogel in a first aqueous gel agent solution for forming a continuous phase of a first hydrogel; and gelling the first aqueous gel agent solution, a temperature of the first aqueous gel agent solution during the dispersion of the second hydrogel being equal to or higher than a solidification point of the first aqueous gel agent solution and lower than a melting point of the second hydrogel.

EXAMPLES

A hydrogel structure was subjected to test evaluation as follows. The configuration and results of the test evaluation of the hydrogel structure are shown in Tables 1 to 4.
(Test Evaluation Method)
<Average Particle Diameter of Hydrogel Particles>

An appropriate amount of hydrogel particles of the agar that became a dispersion phase A was dispersed in deionized water, and the volume-based average particle diameter of the hydrogel particles was measured with a laser diffraction/scattering particle size distribution measuring device (LA-960 available from Horiba, Ltd.). Measurement conditions were such that an index of refraction was 1.2 and the number of test runs N=3. An average of results of three test runs was used as data.

<Breaking Load and Breaking Distortion Factor of Hydrogel Structure>

For comparison of the hardness and brittleness of a hydrogel structure, a continuous phase, and a dispersion phase A, a breaking load and a breaking distortion factor were determined as indications thereof.

For a rectangular hydrogel structure, texture measurement was carried out with a tabletop type physical properties measurement device (TPU-2D available from YAMADEN Co., Ltd.), and the breaking load and the breaking distortion factor were analyzed with texture analysis software included in the device. Measurement conditions were as follows. Data for the breaking load was an average for four test runs. Data for the breaking distortion factor was an average for four test runs. The breaking load of each of the continuous phase and the dispersion phase A was determined using a first aqueous gel agent solution and a second aqueous gel agent solution.

Plunger: No. 6 (diameter $\varphi$: 8 mm)
ACCESSORY: L30
CLEARANCE: 2.0 mm (SET: 20×0.1 mm)
SPEED: 2.5 mm/sec
TIMES: 1
Number of test runs N: 4
Temperature: 25° C.

<Evaluation of Disintegration Properties of Spherical Hydrogel Structure>

For a spherical hydrogel structure, texture measurement was carried out with a tabletop type physical properties measurement device (TPU-2D available from YAMADEN Co., Ltd.), and the breaking load and the breaking distortion factor were analyzed with texture analysis software included in the device. Measurement conditions were as follows. The local minimum value of a load after break was read from a texture curve (a compression distance-load curve) created by texture analysis software, and the ratio of the local minimum value of the load after break to the breaking load (the local minimum value of load after break/the breaking load) was calculated using the local minimum value.

Plunger: No. 1 (diameter $\varphi$: 30 mm)
ACCESSORY: L40
CLEARANCE: 0.3 mm (SET: 3×0.1 mm)
SPEED: 1 mm/sec
TIMES: 1
Number of test runs N: 1
Temperature: 25° C.

<Sensory Evaluation of Disintegration Properties>

Panel consisting of three people evaluated touch when the spherical hydrogel structure was crushed on the palm in sensory evaluation on five levels according to the following evaluation criteria. An average point about the three panels in the sensory evaluation was determined. An average point of 3 points or more was evaluated as A, an average point of 2 points or more and less than 3 points was evaluated as B, and an average point of less than 2 points was evaluated as C.

5: Uniformly collapse
4: Slightly uniformly collapse
3: Neither
2: Slightly nonuniformly collapse
1: Nonuniformly collapse <Evaluation of Storage Stability>

The spherical hydrogel structure was evenly arranged in a sterilization dish, covered with a lid, and stored in a refrigerator set at 4° C. for 3 days. The mass of the hydrogel structure before and after the storage was measured, and a shape retention ratio was calculated from the amount of change in mass by the following expression. The number of test runs N was 18. An average for 18 trials was determined. An average of 90% or more was evaluated as A, and an average of less than 90% was evaluated as C.

Shape retention ratio (%)=(mass after storage/mass before storage)×100

(Hydrogel Structure)

A hydrogel structures were produced as described in Examples 1 to 15 and Comparative Examples 1 to 4. As agar, Ina agar CS-16A (available from Ina Food Industry Co., Ltd., solidification point of 1.5 mass % aqueous solution=34.5° C. to 36.5° C., melting point of 1.5 mass % water-soluble gel=86.0° C. to 90.0° C.) was used.

Examples 1 to 8 and Comparative Example 2

—Production of Hydrogel Particles—

In a 2-L SUS beaker, 985 g of de-ionized water was placed. While the de-ionized water was stirred at the number of revolutions of 400 rpm with a turbine blade having a diameter of 50 mm, 15 g of agar was added and dispersed. Subsequently, the beaker was placed in a water bath set at 92° C., warmed, and kept at a temperature of 85° C. to 92° C. for 15 minutes, to dissolve the agar. Thus, a 1.5 mass % aqueous agar solution was prepared.

Next, the 1.5 mass % aqueous agar solution thus obtained was cooled to 60° C., and the temperature was controlled. 500 mL, which was a half amount, of the aqueous solution was placed in a sprayer having a tank volume of 1 L (SAFETY3 battery-powered sprayer SSD-1 available from Fujiwara Sangyo Co., Ltd.) as a second aqueous gel agent solution containing the agar as a second gel agent.

A plastic sheet was laid over a floor, the 1.5 mass % aqueous agar solution was then sprayed to air above the plastic sheet from a spray nozzle, and cooled and solidified. Thus, hydrogel particles of the agar that became a dispersion phase A of a second hydrogel were produced on the plastic sheet.

—Production of Hydrogel Structure—

In a 100-mL disposable cap, the rest of the 1.5 mass % aqueous agar solution having a liquid temperature kept at 60° C. was placed as a first aqueous gel agent solution for forming a continuous phase of a first hydrogel and the hydrogel particles of the agar heated at 60° C. were placed and dispersed with a spatula such that the amounts of the continuous phase and the dispersion phase A blended were as shown in Tables.

While part of the 1.5 mass % aqueous agar solution containing the hydrogel particles dispersed herein was poured into a cavity of a true-spherical mold having a diameter of 17 mm, the temperature of the mold was adjusted to 4° C., and the aqueous agar solution was cooled for 1 hour, resulting in gelation. Thus, a spherical hydrogel structure shown in Table was produced. Compressed air was applied to an interface between the hydrogel structure and the mold with an air duster (CD-31ECO available from Sanwa Supply Inc.), and the hydrogel structure was separated from the mold and collected. The shape of the hydrogel structure thus obtained was assumed to be the same as the shape of the cavity of the mold. Therefore, the maximum diameter of the spherical hydrogel structure obtained was assumed to be 17 mm.

15 g of each of the first aqueous gel agent solution, the second aqueous gel agent solution, and the 1.5 mass % aqueous agar solution containing the hydrogel particles dispersed herein was placed in a balance dish having a square shape with a side length of 6 cm (BD-2 available from AS ONE Corporation), and allowed to stand at room temperature for 1 hour, resulting in gelation. The gel thus obtained was formed with a spatula into a gel structure having a rectangular shape with a length of 3 cm, a width of 3 cm, and a thickness of 4 mm.

Example 9

A 1.5 mass % aqueous agar solution prepared in the same manner as in Example 1 was placed in a vacuum emulsification disperser (AGI HOMO MIXER Model 2M-05 available from PRIMIX Corporation) as a second aqueous gel agent solution. While the agar aqueous solution was stirred with a first stirrer (HOMO MIXER MARKII2.5 available from PRIMIX Corporation) and a second stirrer (paddle mixer) attached at the number of revolutions of 8000 rpm and 60 rpm, respectively, the aqueous agar solution was ice-cooled and kept at an inner temperature of 35° C. or lower for 60 minutes. Thus, hydrogel particles of the agar that became a dispersion phase A of the second hydrogel were produced. A hydrogel structure shown in Table was produced in the same manner as in Example 7 using the hydrogel particles and the 1.5 mass % aqueous agar solution kept at 60° C.

Example 10

A hydrogel structure shown in Table was produced in the same manner as in Example 9 except that the number of revolutions of the first stirrer was changed to 4000 rpm.

Example 11

A 1.5 mass % aqueous agar solution prepared in the same manner as in Example 1 was taken with a dropper. While 200 g of ice-cooled silicone oil (KF-96A-6CS(-G) available from Shin-Etsu Silicone) was stirred at the number of revolutions of 500 rpm with a turbine blade having a diameter of 50 mm, 50 g of the 1.5 mass % aqueous agar solution set at 60° C. was dropped to the silicone oil from the dropper. Thus, hydrogel particles of the agar that became a dispersion phase A of the second hydrogel was produced in the silicone oil. Subsequently, the silicone oil containing the hydrogel particles was classified through a stainless sieve having a mesh opening of 500 µm (available from TOKYO SCREEN CO., LTD.), and the hydrogel particles collected were washed with water to remove the silicone oil. A hydrogel structure shown in Table was produced in the same manner as in Example 7 using the hydrogel particles and the rest of the 1.5 mass % aqueous agar solution kept at 60° C.

Example 12

A hydrogel structure shown in Table was produced in the same manner as in Example 11 except that the silicone oil containing the hydrogel particles was classified through a stainless sieve having a mesh opening of 1 mm (available from TOKYO SCREEN CO., LTD.).

Example 13

In a 500-mL SUS beaker, 288.75 g of de-ionized water was placed. While the de-ionized water was stirred at the number of revolutions of 200 rpm with a turbine blade having a diameter of 50 mm, 6.75 g of agar and 4.5 g of surfactant (NIKKOL SMT (sodium methyl stearoyl taurate) available from Nikko Chemicals Co., Ltd.) were added and dispersed. Subsequently, the beaker was placed in a water bath set at 92° C., warmed, and kept at a temperature of 85° C. to 92° C. for 15 minutes, to dissolve the agar. Thus, a 2.25 mass % aqueous agar solution was prepared.

Next, the 2.25 mass % aqueous agar solution thus obtained was cooled to 60° C., the temperature was controlled, and the aqueous solution was placed in an ultra-high speed multi-use mixing system (LABOLUTION available from PRIMIX Corporation). To the aqueous solution, 100 g of silicone oil (KF-96A-6CS(-G) available from Shin-Etsu Silicone) that became dispersion particles B set at 60° C. was added. The mixture was stirred at the number of revolutions of 6000 rpm for 1 minute with an attached stirrer (HOMO MIXER MARKII2.5 available from PRIMIX Corporation), to prepare a 2.25 mass % agar emulsion liquid containing the silicone oil dispersed herein. The volume average particle diameter of the silicone oil, measured with a laser diffraction/scattering particle size distribution measuring device (LA-960 available from Horiba, Ltd.) was 9 μm.

In a 100-mL disposable cup, 75 g of the agar emulsion liquid kept at 60° C. was placed, and 25 g of agar hydrogel particles prepared in the same manner as in Example 1 and heated at 60° C. were placed and dispersed with a spatula. A hydrogel structure shown in Table was produced in the same manner as in Example 7 using this liquid.

Example 14

In a 5-L SUS beaker, 3860 g of de-ionized water was placed. While the de-ionized water was stirred at the number of revolutions of 400 rpm with a turbine blade having a diameter of 50 mm, 140 g of agar was added and dispersed. Subsequently, the beaker was placed in a water bath set at 92° C., warmed, and kept at a temperature of 85° C. to 92° C. for 15 minutes, to dissolve the agar. Thus, a 3.5 mass % aqueous agar solution was prepared.

Subsequently, the 3.5% aqueous agar solution thus obtained was kept at 80° C., is then caused to, at an output of 95 Hz, pass through a rotational positive displacement uniaxial eccentric screw pump (MOHNO PUMP 2NL10F available from HEISHIN LTd.) through which de-ionized water of 80° C. had been passed to increase a temperature, sprayed into a spray tank having a volume of 4 m³ from a two-fluid nozzle (Nozzle No. SUE45B available from Spraying Systems Co.), and then cooled and solidified. Thus, hydrogel particles of the agar that became a dispersion phase A of a second hydrogel were produced. In this state, the spray flow rate was 12 kg/h, the air flow rate was 27 m³/h, and the air pressure was 0.4 MPa.

A hydrogel structure shown in Table was produced in the same manner as in Example 7 using the hydrogel particles and a 1.5 mass % aqueous agar solution kept at 60° C.

Example 15

A hydrogel structure shown in Table was produced in the same manner as in Example 7 except that a dispersion phase A was produced using an aqueous agar solution having the same composition as that of the dispersion phase A shown in Table.

Comparative Example 1

A hydrogel structure including only a continuous phase was produced in the same manner as in Example 1 except that only a 1.5 mass % aqueous agar solution containing no hydrogel particles was used.

Comparative Example 3

A hydrogel structure including only a continuous phase was produced in the same manner as in Comparative Example 1 except that a 0.5 mass % aqueous agar solution was used.

Comparative Example 4

A hydrogel structure containing only a continuous phase was produced in the same manner as in Comparative Example 1 except that a 3.0 mass % aqueous agar solution was used.

As seen from the experimental results described above, the hydrogel structures of Examples of the present invention were more excellent in disintegration properties and storage stability than the hydrogel structures of Comparative Examples. In contrast, the hydrogel structure including no dispersion phase of the second hydrogel dispersed in the continuous phase cannot ensure storage stability even when the breaking load was decreased to achieve allowable disintegration properties (Comparative Example 3).

TABLE 1

| | | | Examples | | | | | | | | Comparative Examples | |
|---|---|---|---|---|---|---|---|---|---|---|---|---|
| | | | 1 | 2 | 3 | 4 | 5 | 6 | 7 | 8 | 1 | 2 |
| Continuous phase | Composition (mass %) | Water | 98.5 | 98.5 | 98.5 | 98.5 | 98.5 | 98.5 | 98.5 | 98.5 | 98.5 | 98.5 |
| | | Agar | 1.5 | 1.5 | 1.5 | 1.5 | 1.5 | 1.5 | 1.5 | 1.5 | 1.5 | 1.5 |
| | Breaking load (N) | | 5.7 | 5.7 | 5.7 | 5.7 | 5.7 | 5.6 | 5.6 | 5.6 | 5.6 | 5.7 |
| Dispersion phase A | Composition (mass %) | Water | 98.5 | 98.5 | 98.5 | 98.5 | 98.5 | 98.5 | 98.5 | 98.5 | — | 98.5 |
| | | Agar | 1.5 | 1.5 | 1.5 | 1.5 | 1.5 | 1.5 | 1.5 | 1.5 | — | 1.5 |
| | Average particle diameter (μm) | | 341 | 341 | 341 | 341 | 341 | 400 | 400 | 400 | — | 341 |
| | Breaking load (N) | | 5.7 | 5.7 | 5.7 | 5.7 | 5.7 | 5.6 | 5.6 | 5.6 | — | 5.7 |
| Hydrogel structure | Blending ratio (mass %) | Continuous phase | 95 | 90 | 85 | 80 | 75 | 75 | 50 | 25 | 100 | 99 |
| | | Dispersion phase A | 5 | 10 | 15 | 20 | 25 | 25 | 50 | 75 | 0 | 1 |

TABLE 1-continued

| | | | Examples | | | | | | | | Comparative Examples | |
|---|---|---|---|---|---|---|---|---|---|---|---|---|
| | | | 1 | 2 | 3 | 4 | 5 | 6 | 7 | 8 | 1 | 2 |
| | Composition (mass %) | Water | 98.5 | 98.5 | 98.5 | 98.5 | 98.5 | 98.5 | 98.5 | 98.5 | 98.5 | 98.5 |
| | | Agar | 1.5 | 1.5 | 1.5 | 1.5 | 1.5 | 1.5 | 1.5 | 1.5 | 1.5 | 1.5 |
| | Breaking load (N) | | 4.9 | 4.3 | 3.8 | 3.4 | 3.0 | 3.2 | 1.5 | 0.3 | 5.6 | 5.5 |
| | Breaking distortion factor (%) | | 34 | 33 | 32 | 30 | 28 | 30 | 24 | 9 | 36 | 37 |
| Spherical hydrogel structure | Maximum diameter (mm) | | 17 | 17 | 17 | 17 | 17 | 17 | 17 | 17 | 17 | 17 |
| | Maximum diameter/ average particle diameter of dispersion phase A | | 49.9 | 49.9 | 49.9 | 49.9 | 49.9 | 42.5 | 42.5 | 42.5 | — | 49.9 |
| | Breaking load (N) | | 2.9 | 2.4 | 2.1 | 1.8 | 1.5 | 2.0 | 1.1 | 0.2 | 5.3 | 3.8 |
| | Minimum value of load after break (N) | | 0.89 | 0.65 | 0.67 | 0.62 | 0.51 | 0.59 | 0.61 | 0.17 | 0.41 | 0.36 |
| | Minimum value of load after break/ breaking load | | 0.31 | 0.27 | 0.33 | 0.35 | 0.33 | 0.29 | 0.54 | 0.80 | 0.079 | 0.094 |
| | Breaking distortion factor (%) | | 26 | 24 | 23 | 22 | 23 | 23 | 21 | 6 | 33 | 28 |
| Disintegration properties | Sensory evaluation average point | | 2.7 | 2.7 | 3.3 | 3.3 | 3.7 | 3.7 | 4.0 | 4.3 | 1.3 | 1.7 |
| | Evaluation | | B | B | A | A | A | A | A | A | C | C |
| Storage stability | Average shape retention ratio (%) after 3 days | | 99 | 99 | 99 | 99 | 99 | 99 | 97 | 97 | 98 | 99 |
| | Evaluation | | A | A | A | A | A | A | A | A | A | A |

TABLE 2

| | | | Examples | | | | |
|---|---|---|---|---|---|---|---|
| | | | 9 | 10 | 7 | 11 | 12 |
| Continuous phase | Composition (mass %) | Water | 98.5 | 98.5 | 98.5 | 98.5 | 98.5 |
| | | Agar | 1.5 | 1.5 | 1.5 | 1.5 | 1.5 |
| | Breaking load (N) | | 5.6 | 5.6 | 5.6 | 5.6 | 5.6 |
| Dispersion phase A | Composition (mass %) | Water | 98.5 | 98.5 | 98.5 | 98.5 | 98.5 |
| | | Agar | 1.5 | 1.5 | 1.5 | 1.5 | 1.5 |
| | Average particle diameter (μm) | | 25 | 45 | 400 | 707 | 1500 |
| | Breaking load (N) | | 5.6 | 5.6 | 5.6 | 5.6 | 5.6 |
| Hydrogel structure | Blending ratio (mass %) | Continuous phase | 50 | 50 | 50 | 50 | 50 |
| | | Dispersion phase A | 50 | 50 | 50 | 50 | 50 |
| | Composition (mass %) | Water | 98.5 | 98.5 | 98.5 | 98.5 | 98.5 |
| | | Agar | 1.5 | 1.5 | 1.5 | 1.5 | 1.5 |
| | Breaking load (N) | | 1.7 | 1.5 | 1.5 | 1.8 | 2.0 |
| | Breaking distortion factor (%) | | 27 | 24 | 24 | 24 | 25 |
| Spherical hydrogel structure | Maximum diameter (mm) | | 17 | 17 | 17 | 17 | 17 |
| | Maximum diameter/ average particle diameter of dispersion phase A | | 680 | 378 | 42.5 | 24.0 | 11.3 |
| | Breaking load (N) | | 1.8 | 1.2 | 1.1 | 1.2 | 1.4 |
| | Minimum value of load after break (N) | | 0.17 | 0.17 | 0.61 | 0.46 | 0.46 |
| | Minimum value of load after break/ breaking load | | 0.10 | 0.14 | 0.54 | 0.38 | 0.33 |
| | Breaking distortion factor (%) | | 23 | 20 | 21 | 22 | 21 |

TABLE 2-continued

| | | | Examples | | | |
| --- | --- | --- | --- | --- | --- | --- |
| | | 9 | 10 | 7 | 11 | 12 |
| Disinte-gration properties | Sensory evaluation average point | 4.0 | 3.7 | 4.0 | 4.3 | 4.3 |
| | Evaluation | A | A | A | A | A |
| Storage stability | Average shape retention ratio (%) after 3 days | 97 | 97 | 97 | 98 | 98 |
| | Evaluation | A | A | A | A | A |

TABLE 3

| | | | Examples | |
| --- | --- | --- | --- | --- |
| | | | 7 | 13 |
| Continuous phase | Composition (mass %) | Water | 98.5 | 96.25 |
| | | Agar | 1.5 | 2.25 |
| | | Surfactant | — | 1.50 |
| | | Breaking load (N) | 5.6 | 8.8 |
| Dispersion phase A | Composition (mass %) | Water | 98.5 | 98.5 |
| | | Agar | 1.5 | 1.5 |
| | | Average particle diameter (μm) | 400 | 400 |
| | | Breaking load (N) | 5.6 | 5.6 |
| Dispertion particles B | Composition (mass %) | Silicone oil | — | 100 |
| | | Average particle diameter (μm) | — | 9 |
| Hydrogel structure | Blending ratio (mass %) | Continuous phase | 50 | 50 |
| | | Dispersion phase A | 50 | 25 |
| | | Dispertion particles B | — | 25 |
| | Composition (mass %) | Water | 98.5 | 72.75 |
| | | Agar | 1.5 | 1.50 |
| | | Silicone oil | — | 25.00 |
| | | Surfactant | — | 0.75 |
| | | Breaking load (N) | 1.5 | 1.0 |
| | | Breaking distortion factor (%) | 24 | 20 |
| | Spherical hydrogel structure | Maximum diameter (mm) | 17 | 17 |
| | | Maximum diameter/average particle diameter of dispersion phase A | 42.5 | 42.5 |
| | | Breaking load (N) | 1.1 | 0.83 |
| | | Minimum value of load after break (N) | 0.61 | 0.52 |
| | | Minimum value of load after break/ breaking load | 0.54 | 0.63 |
| | | Breaking distortion factor (%) | 21 | 18 |
| | Disintegration properties | Sensory evaluation average point | 4.0 | 5.0 |
| | | Evaluation | A | A |
| | Storage stability | Average shape retention ratio (%) after 3 days | 97 | 100 |
| | | Evaluation | A | A |

TABLE 4

| | | | Examples | | | Comparative Examples | |
| --- | --- | --- | --- | --- | --- | --- | --- |
| | | | 7 | 14 | 15 | 3 | 4 |
| Continuous phase | Composition (mass %) | Water | 98.5 | 98.5 | 97.0 | 99.5 | 97.0 |
| | | Agar | 1.5 | 1.5 | 3.0 | 0.5 | 3.0 |
| | | Breaking load (N) | 5.6 | 5.6 | 13.1 | 0.7 | 12.3 |
| Dispersion phase A | Composition (mass %) | Water | 98.5 | 96.5 | 98.5 | — | — |
| | | Agar | 1.5 | 3.5 | 1.5 | — | — |

TABLE 4-continued

| | | | Examples | | | Comparative Examples | |
| --- | --- | --- | --- | --- | --- | --- | --- |
| | | | 7 | 14 | 15 | 3 | 4 |
| | Average particle diameter (μm) | | 400 | 141 | 400 | — | — |
| | Breaking load (N) | | 5.6 | 13.1 | 5.6 | — | — |
| Hydrogel structure | Blending ratio (mass %) | Continuous phase | 50 | 50 | 50 | 100 | 100 |
| | | Dispersion phase A | 50 | 50 | 50 | 0 | 0 |
| | Composition (mass %) | Water | 98.5 | 97.5 | 97.75 | 99.5 | 97.0 |
| | | Agar | 1.5 | 2.5 | 2.25 | 0.5 | 3.0 |
| | Breaking load (N) | | 1.5 | 1.4 | 5.0 | 0.7 | 12.3 |
| | Breaking distortion factor (%) | | 24 | 17 | 28 | 26 | 39 |
| Spherical hydrogel structure | Maximum diameter (mm) | | 17 | 17 | 17 | 17 | 17 |
| | Maximum diameter/ average particle diameter of dispersion phase A | | 42.5 | 121 | 42.5 | — | — |
| | Breaking load (N) | | 1.1 | 1.1 | 3.2 | 1.8 | 13.6 |
| | Minimum value of load after break - analytical value (N) | | 0.61 | 0.13 | 1.14 | 0.17 | 0.87 |
| | Minimum value of load after break/ breaking load | | 0.54 | 0.12 | 0.36 | 0.099 | 0.064 |
| | Breaking distortion factor (%) | | 21 | 17 | 26 | 26 | 35 |
| Disinte- gration properties | Sensory evaluation average point | | 4.0 | 5.0 | 3.5 | 2.7 | 1.0 |
| | Evaluation | | A | A | A | B | C |
| Storage stability | Average shape retention ratio (%) after 3 days | | 97 | 98 | — | 80 | 99 |
| | Evaluation | | A | A | — | C | A |

INDUSTRIAL APPLICABILITY

The present invention is useful in a technical field of a hydrogel structure, a method for producing the same, a cosmetic product composition containing the same, and use of the same as a cosmetic product.

DESCRIPTION OF REFERENCE CHARACTERS

10 Hydrogel Structure
11 Continuous Phase
12 Dispersion Phase A
13 Dispersion Particles B
14 Dispersion Particles C

The invention claimed is:

1. A hydrogel structure comprising:
a continuous phase of a first hydrogel; and
a dispersion phase of a second hydrogel, the dispersion phase being dispersed in the continuous phase,
a ratio of a local minimum value of a load after break to a breaking load (a local minimum value of a load after break/a breaking load) being 0.1 or more.

2. The hydrogel structure of claim 1, wherein a maximum diameter is from 500 μm to 40 mm inclusive.

3. The hydrogel structure of claim 1, wherein a content of the dispersion phase is from 3 mass % to 99 mass % inclusive.

4. The hydrogel structure of claim 1, wherein a content of the continuous phase is from 1 mass % to 97 mass % inclusive.

5. The hydrogel structure of claim 1, wherein a gel agent used to obtain the first hydrogel comprises a water-soluble uncrosslinked polymer.

6. The hydrogel structure of claim 1, wherein a gel agent used to obtain the second hydrogel comprises a water-soluble uncrosslinked polymer.

7. The hydrogel structure of claim 1, wherein a gel agent used to obtain the first hydrogel and a gel agent used to obtain the second hydrogel include agar.

8. The hydrogel structure of claim 1, wherein a gel agent used to obtain the first hydrogel is the same as a gel agent used to obtain the second hydrogel.

9. The hydrogel structure of claim 1, wherein a ratio of a maximum diameter of the hydrogel structure to an average particle diameter of the dispersion phase is from 1 to 50000 inclusive.

10. The hydrogel structure of claim 1, wherein an average particle diameter of the dispersion phase is from 1 μm to 5 mm inclusive.

11. The hydrogel structure of claim 1, wherein a breaking distortion factor of the hydrogel structure is 50% or less.

12. The hydrogel structure of claim 1, wherein a breaking load of the hydrogel structure is from 0.1 N to 30 N inclusive.

13. The hydrogel structure of claim 1, wherein one or both of the continuous phase and the dispersion phase comprise an emulsifying dispersant.

14. The hydrogel structure of claim 1, further comprising dispersion particles different from the dispersion phase dispersed in the continuous phase.

15. The hydrogel structure of claim 1, wherein the hydrogel structure has a particulate shape.

16. The hydrogel structure of claim 1, wherein a content of a first gel agent in the continuous phase is from 0.8 mass % to 20 mass % inclusive.

17. The hydrogel structure of claim 1, wherein a content of a second gel agent in the dispersion phase is from 0.8 mass % to 10 mass % inclusive.

18. The hydrogel structure of claim 1, wherein composition of the first hydrogel is the same as composition of the second hydrogel.

19. The hydrogel structure of claim 1, wherein the ratio the local minimum value of the load after break to the breaking load (the local minimum value of the load after break/the breaking load) is 1 or less.

20. A cosmetic product composition comprising the hydrogel structure of claim 1.

21. A method for producing the hydrogel structure of claim 1, the method comprising:

dispersing hydrogel particles that become the dispersion phase of the second hydrogel in a first aqueous gel agent solution for forming the continuous phase of the first hydrogel; and gelling the first aqueous gel agent solution.

22. A hydrogel structure comprising:

a continuous phase of a first hydrogel; and a dispersion phase of a second hydrogel, the dispersion phase being dispersed in the continuous phase, wherein a mass ratio of the dispersion phase to the continuous phase (the dispersion phase/the continuous phase) is more than 1/99 and 99/1 or less.

23. A method for producing a hydrogel structure comprising:

dispersing a second hydrogel in a first aqueous gel agent solution for forming a continuous phase of a first hydrogel; and gelling the first aqueous gel agent solution, a temperature of the first aqueous gel agent solution during the dispersion of the second hydrogel being equal to or higher than a solidification point of the first aqueous gel agent solution and lower than a melting point of the second hydrogel.

* * * * *